US00PP20720P2

(12) United States Plant Patent
Meilland

(10) Patent No.: US PP20,720 P2
(45) Date of Patent: Feb. 2, 2010

(54) FLORIBUNDA ROSE PLANT NAMED 'MEIBIVERS'

(50) Latin Name: *Rosa hybrida*
Varietal Denomination: Meibivers

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/314,301

(22) Filed: Dec. 8, 2008

(30) Foreign Application Priority Data

Oct. 27, 2008 (EM) ..... 2008/2338

(51) Int. Cl.
*A01H 5/00* (2006.01)

(52) U.S. Cl. ..... Plt./141

(58) Field of Classification Search ..... Plt./141
See application file for complete search history.

*Primary Examiner*—Annette H Para
(74) *Attorney, Agent, or Firm*—Buchanan Ingersoll & Rooney PC

(57) ABSTRACT

A new and distinct Floribunda rose plant is provided which forms attractive small red-purple blossoms that commonly are darker in coloration at the margins and veins. The plant exhibits strong vegetation, a bushy growth habit, and dark green foliage with a semi-glossy aspect. The disease resistance is good particularly with respect to Marsonia. The attractive dark green foliage contrasts nicely with the red-purple blossom coloration. The new variety is well suited for growing as attractive ornamentation in parks and gardens.

1 Drawing Sheet

Figures 1, 2, 3, 4, 5, 6, 7, 8, 9, 10, 11, 12, 13, 14, 15, 16:
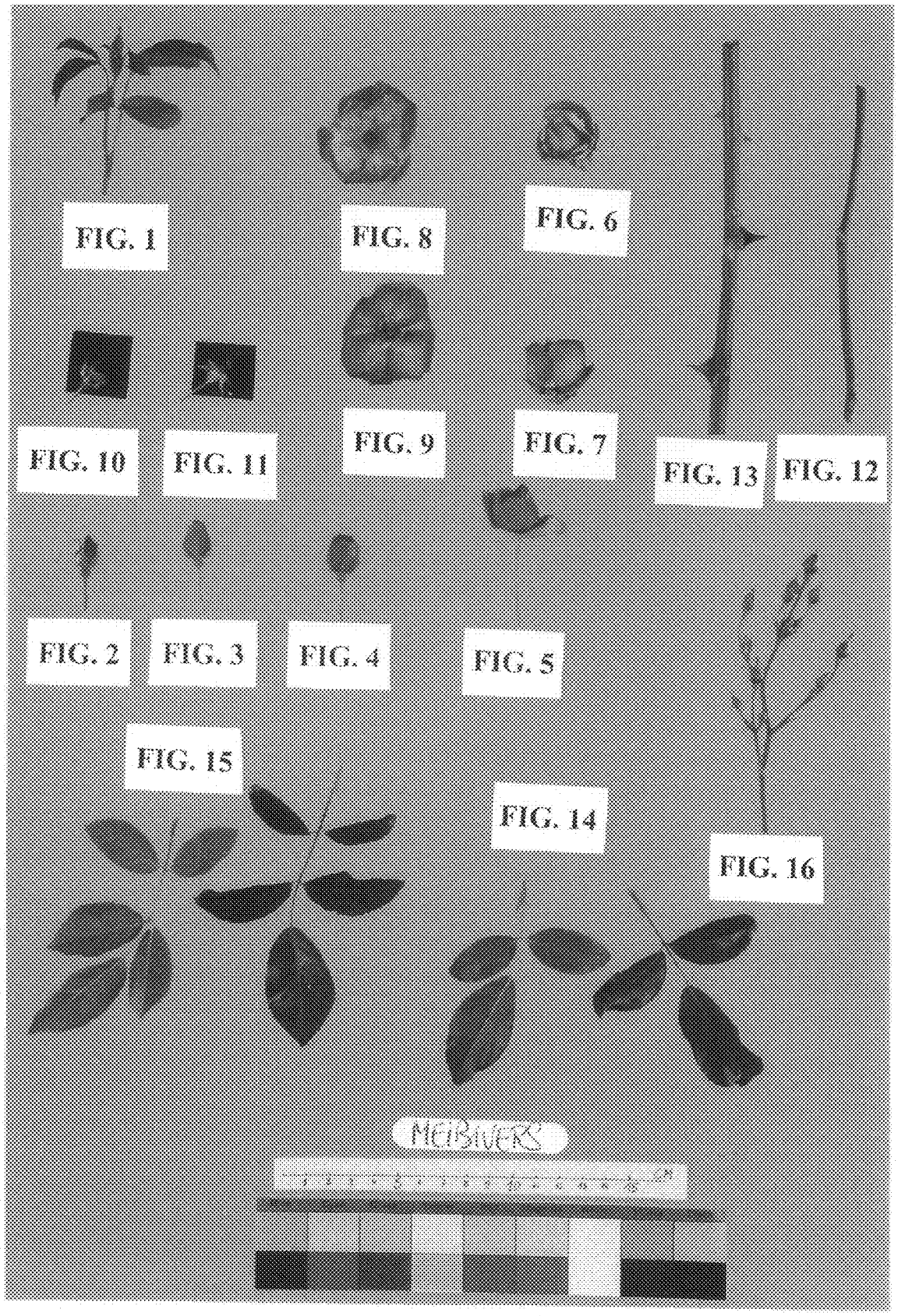

Botanical/commercial classification: *Rosa hybrida*/Floribunda Rose Plant.

Varietal denomination: cv. Meibivers.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was a product of the cross of the 'Korimro' variety (non-patented in the United States) and the 'Noatraum' variety (U.S. Plant Pat. No. 7,282). The male parent (i.e., the pollen parent) was the 'Applejack' variety (non-patented in the United States). The 'Korimro' variety is marketed under the IMMENSEE trademark, and the 'Noatraum' variety is marketed under the FLOWER CARPET and HEIDETRAUM trademarks. The parentage of the new variety can be summarized as follows:

('Korimro'×'Noatraum')×'Applejack'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy growth habit,
(b) abundantly forms attractive small red-purple blossoms that commonly are darker in coloration at the veins and margins,
(c) forms attractive dark green semi-glossy foliage that contrasts nicely with the blossom coloration,
(d) displays excellent resistance to Marsonia, and
(e) is well suited for growing as ornamentation in parks and gardens.

The new variety well meets the needs of the horticultural industry and can be grown to advantage in the landscape where attractive ornamentation is desired.

The new variety can be readily distinguished from its ancestors. For instance, the Korimro' variety displays white blossoms. The 'Noatraum' variety displays dark pink blossoms. The 'Applejack' variety forms neyron rose stippled crimson blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meibivers'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during October while budded on *Rosa froebelli* understock and growing outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—under surface (left), and—pper surface (right);

FIG. 15—illustrates a specimen of a leaf with five leaflets—plan view—under surface (left), and—upper surface (right); and;

FIG. 16—illustrates a specimen of a cluster of buds.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of one-year-old plants during May while growing on their own roots outdoors at Le Cannet des Maures, Var, France.

Class: Floribunda.

Plant:

*Habit.*—Bushy.

Branches:

*Color.*—Young stems: near Yellow-Green Group 146B. Adult wood: near Green Group 138A.

*Thorns.*—On young stems: Small prickles: commonly absent. Long prickles: configuration: upright and very longish-pointed on the upper surface, slightly concave on the under surface, and narrow and short at the base. quantity: approximately 5 on average on a stem length of 10 cm. length: approximately 1.1 cm on average. color: near Greyed-Red Group 181A. On adult stems: Small prickles: commonly absent. Long prickles: configuration: upright and very longish-pointed on the upper surface, slightly concave on the under surface, and narrow and short at the base. quantity: approximately 5 on average on a stem length of 18 cm. length: approximately 1.1 cm on average. color: near Greyed-Orange Group 176B.

Leaves:

*Stipules.*—Adnate, pectinate, and narrow, approximately 1.3 cm in length on average, approximately 0.5 cm in width on average, near Yellow-Green Group 144A on the upper surface, and near Yellow-Green Group 143C on the under surface.

*Petioles.*—Upper surface: near Yellow-Green Group 147A in coloration. Under surface: near Green Group 141C in coloration. Texture: non-glandular and commonly bear some prickles. Length: approximately 3.4 cm for the terminal leaflet.

*Rachis.*—Upper surface: near Yellow-Green Group 147A in coloration. Under surface: near Green Group 141C in coloration. Texture: commonly bear some prickles.

*Leaflets.*—Number: 3, 5 (most often), and 7. Shape: generally oval with a rounded base and an acuminate tip. Size: the terminal leaflets commonly are approximately 4.1 cm in length on average, and approximately 2.5 cm in width on average. Serration: small and single (as illustrated). Texture: somewhat flexible and semi-glossy on the upper surface. General appearance: rather dense. Color (young foliage): upper surface: near Green Group 141B. under surface: near Green Group 143C. Color (adult foliage): upper surface: near Green Group 139A. under surface: near Yellow-Green Group 146B.

Inflorescence:

*Number of flowers.*—Pluriflorous, commonly approximately 3 to 7 flowers per stem.

*Peduncle.*—Smooth, near Greyed-Purple Group 185A in coloration, approximately 5.5 cm in length on average, and approximately 0.2 cm in diameter on average.

*Sepals.*—Upper surface: smooth and near Yellow-Green Group 146D in coloration. Under surface: smooth and near Yellow-Green Group 144A in coloration. Configuration: approximately 2 cm in length on average, approximately 0.5 cm in width on average at the widest point, and longish-pointed at the tip and narrow with an upright base.

*Buds.*—Shape: ovoid. Size: small. Length: approximately 1.3 cm on average. Width: approximately 1 cm on average at the widest point. Color: upper surface: near Red Group 36B suffused with Red-Purple Group 62C as the calyx breaks. under surface: near Red-Purple Group 63B as the calyx breaks.

*Flower.*—Shape: cup-shaped. Diameter: approximately 4 cm on average. Color (in the course of opening): upper surface: near Red-Purple Group 65C. under surface: near Red-Purple Group 72C. Color (when fully open): upper surface: near Red-Purple Group 65B, and generally veined and margined with near darker Red-Purple Group 72C. under surface: near Red-Purple Group 70B, and generally veined and margined with near Red-Purple Group 71C. Fragrance: none. Petal number: commonly approximately 24 to 27 on average under normal growing conditions. Petal shape: generally with a rounded tip and rounded base. Petal size: commonly approximately 2.5 cm in length on average, and approximately 2.5 cm in width on average. Petal texture: flexible. Petal arrangement: imbricated, and without petaloids. Petal drop: good with the petals commonly detaching cleanly before drying. Stamen number: approximately 106 on average. Anthers: regularly arranged around the styles, approximately 0.2 cm in size on average, and near Yellow-Orange Group 22A in coloration. Pollen: present. Filaments: approximately 0.6 cm in length on average, and near Yellow Group 4C in coloration. Pistils: approximately 34 on average. Stigmas: approximately 0.1 cm in size on average, and near Greyed-Red Group 181A in coloration. Styles: approximately 0.5 cm in length on average, and near Greyed-Red Group 180A in coloration. Receptacle: smooth, pitcher-shaped in longitudinal section, approximately 0.5 cm in length on average, approximately 0.5 cm in width on average at the widest point, and near Greyed-Purple Group 184A in coloration.

Development:

*Vegetation.*—Strong.

*Blooming.*—Medium season, very abundant and substantially continuous.

*Resistance to diseases.*—Good, particularly with respect to Marsonia.

I claim:

1. A new and distinct Floribunda rose plant characterized by the following combination of characteristics:

(a) exhibits a bushy growth habit, (b) abundantly forms attractive small red-purple blossoms that commonly are darker in coloration at the veins and margins, (c) forms attractive dark green semi-glossy foliage that contrasts nicely with the blossom coloration, (d) displays excellent resistance to Marsonia, and (e) is well suited for growing as ornamentation in parks and gardens;

substantially as herein shown and described.

* * * * *

NEBIVERS